US00PP22493P3

(12) United States Plant Patent

Maillard et al.

(10) Patent No.: US PP22,493 P3

(45) Date of Patent: Feb. 14, 2012

(54) NECTARINE TREE NAMED 'NECTAVANTOP'

(50) Latin Name: ***Prunus persica* var. nucipersica**
Varietal Denomination: NECTAVANTOP

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/662,968

(22) Filed: May 13, 2010

(65) Prior Publication Data

US 2010/0293678 P1 Nov. 18, 2010

(30) Foreign Application Priority Data

May 18, 2009 (QZ) ..... 20090928

(51) Int. Cl.
*A01H 5/00* (2006.01)

(52) U.S. Cl. ..... Plt./190

(58) Field of Classification Search ..... Plt./190
See application file for complete search history.

*Primary Examiner* — June Hwu

(74) *Attorney, Agent, or Firm* — Westerman, Hattori, Daniels & Adrian, LLP

(57) ABSTRACT

A new and distinct variety of nectarine tree, denominated 'NECTAVANTOP', has fruits of very long shelf life without alteration before and after harvesting, a semi-sweet yellow flesh of high-eating quality and an attractive red skin. Fruits can be consumed crunchy or melting.

4 Drawing Sheets

Botanical classification: *Prunus persica* var. nucipersia.

Variety denomination: 'NECTAVANTOP'.

This application claims priority of Community plant variety right No. 2009/0928 filed on May 18, 2009, which is hereby incorporated by reference in its entirety.

BACKGROUND OF THE VARIETY

The present invention relates to a new and distinct variety of *Prunus persica* var. nucipersica yellow nectarine tree, which has been given the denomination 'NECTAVANTOP'. This tree, named 'NECTAVANTOP', produces clingstone fruits of good eating quality for fresh market in middle June in the 66 - Pyrénées-Orientales departement —France. Contrast is made to 'Nectalady' (U.S. Plant Pat. No. 17,580), 'Nectapink' (U.S. Plant Pat. No. 17,584) and 'Redlatenecta' (non-patented) yellow nectarine trees, standard varieties, for reliable description. 'NECTAVANTOP' is a promising candidate for commercial success in that it has an evenness of maturity, and produces regular fruits in large quantity and with a high productivity. It was chosen because of its hardiness and fruit lifetime before and after harvest, and because of its aromatic semi sweet taste.

ORIGIN OF THE VARIETY

'NECTAVANTOP' nectarine tree originated in a cultivated area of the south of France, in the 66 - Pyrénées-Orientales departement - France where it was tested. This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontagne': it dries the air, clears the sky from clouds, but its intensity can be strong and affect the harvest, fruit quantity and/or quality.

Marine moisture does not affect the place. Precipitations are irregular through the year and from one year to another. The amount of rainy days does not exceed 80 days per year, and are mostly in Spring and Autumn. In May and October, very intense precipitations occasionally happen. Summer is dry with a few thunderstorms.

The 'NECTAVANTOP' variety was selected from controlled crosses between the 'Redlatenecta' (non-patented) yellow nectarine tree (female parent) and the 'Nectalady' (U.S. Plant Pat. No. 17,580) yellow nectarine tree (male parent). 'NECTAVANTOP' was provisionally designated, tested and genetically identified by a genetic profile, as 05.06.183 NJ and was registered at the Official Catalogue of the Agriculture Ministry of the French Republic on Dec. 1, 2008 under number 1028954. It was obtained by hybridizing and propagated by grafting on 'Franc Inra Montclar' (non-patented), 'Cadaman' (non-patented) or 'INRA GF 677' (non-patented) rootstock trees. It has been determined to have unique tree and fruit characteristics making it worthy for commercial fresh fruit production. There are no known effects of the rootstock varieties set forth above on the scion cultivar. Asexually propagated plants remained true to the original tree and all characteristics of the tree and the fruit were transmitted. The plant was reproduced asexually by us in Les Regalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of nectarine tree blooms in March at Perpignan in the Pyrénées-Orientales departement, France. More particularly, it generally blooms between March $5^{th}$ and March $16^{th}$, generally about one day later than 'Nectapink' (U.S. Plant Pat. No. 17,584).

The first fruit of 'NECTAVANTOP' ripens in August, generally approximately at the same time than 'Nectapink' (U.S.

Plant Pat. No. 17,584). More particularly, it approximately ripens between August 1st and August 10th under normal climatic conditions.

DESCRIPTION OF THE DRAWINGS

In the accompanying drawing, which are as nearly true as it is reasonably possible to make in a color illustration of this type.

Figure 1:
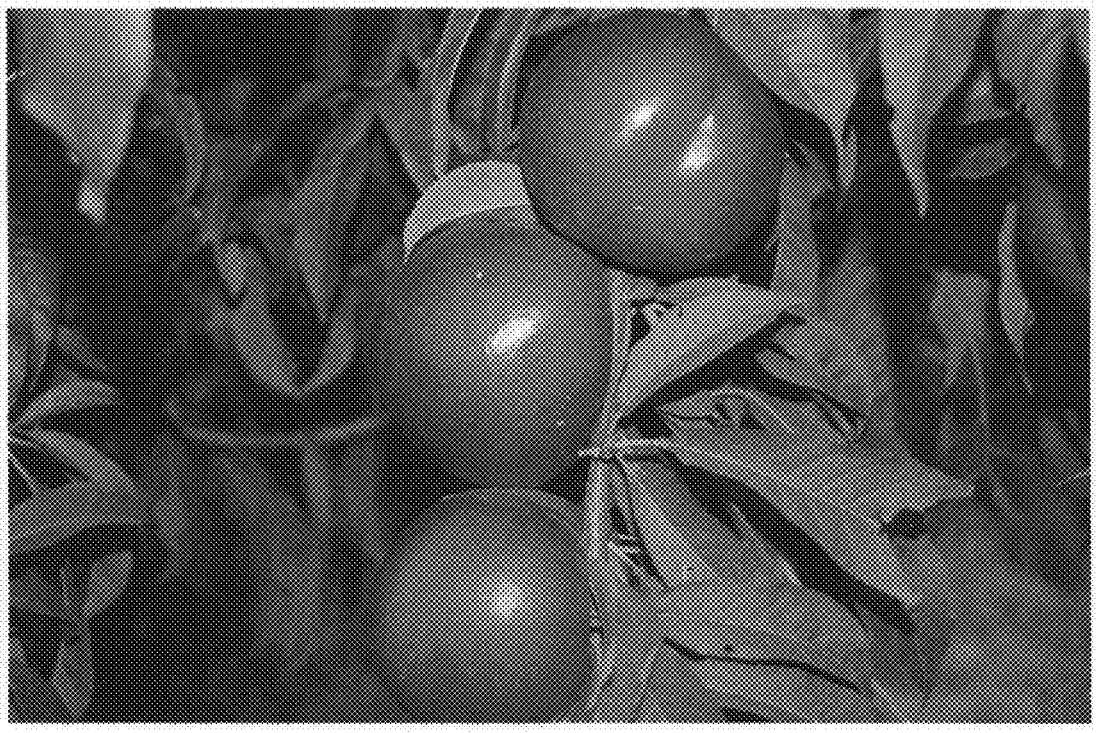
FIG. 1 is a color photograph, which shows typical fruit specimens on a tree of the new variety and leaves of the new variety in orchard.
Figure 2:
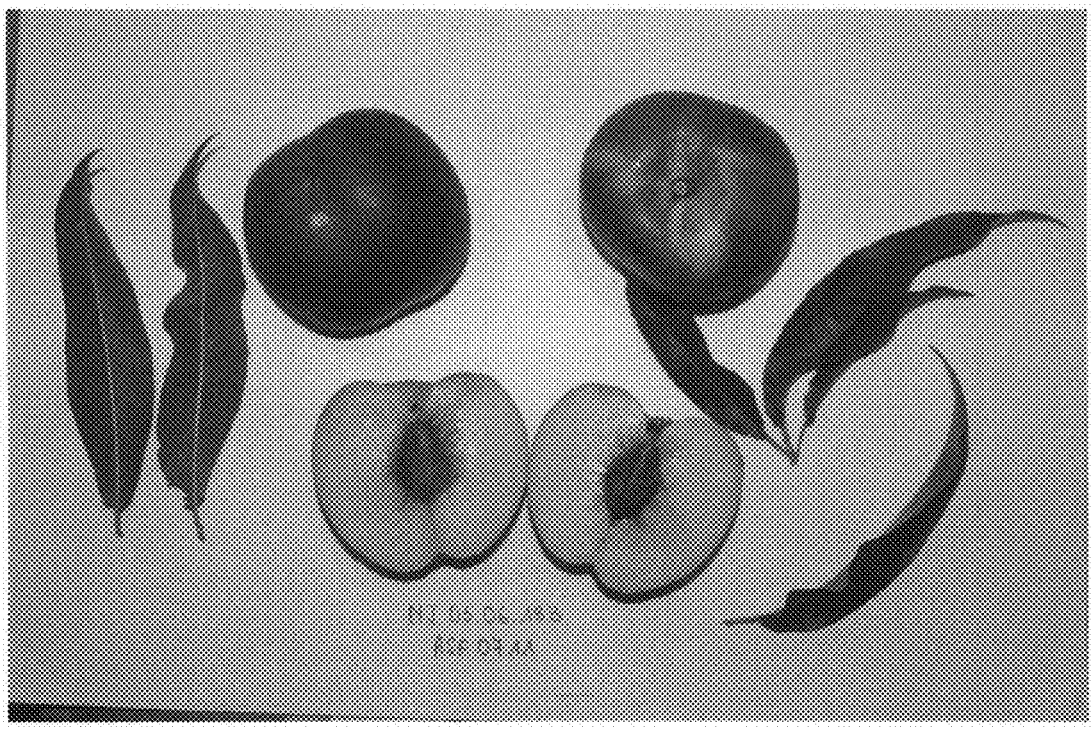
FIG. 2 is a color photograph, which shows two whole fruits of the new variety and leaves of the new variety, with a third fruit cut in half with the pit left in one of the halves for depicting the fruit flesh, the pit cavity and the stone of the new variety.
Figure 3:
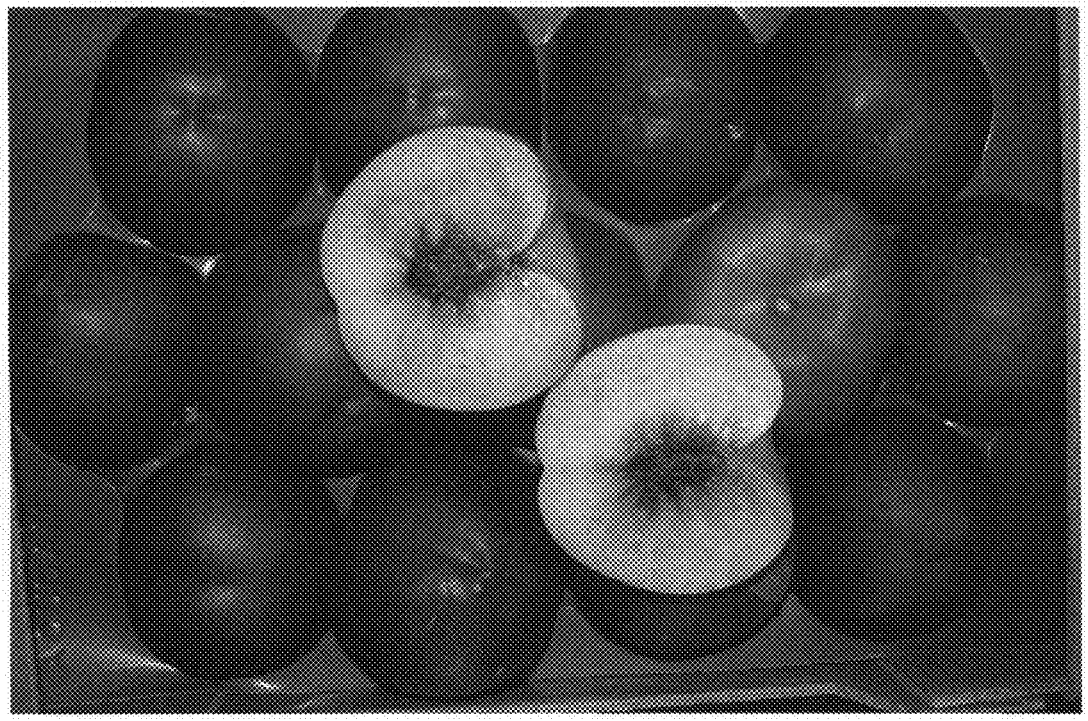
FIG. 3 is a color photograph, which shows a box of fruits sufficiently mature for shipment and a fruit cut in half with the pit left in one of the halves for depicting the fruit flesh, the pit cavity and the stone of the new variety.
Figure 4:
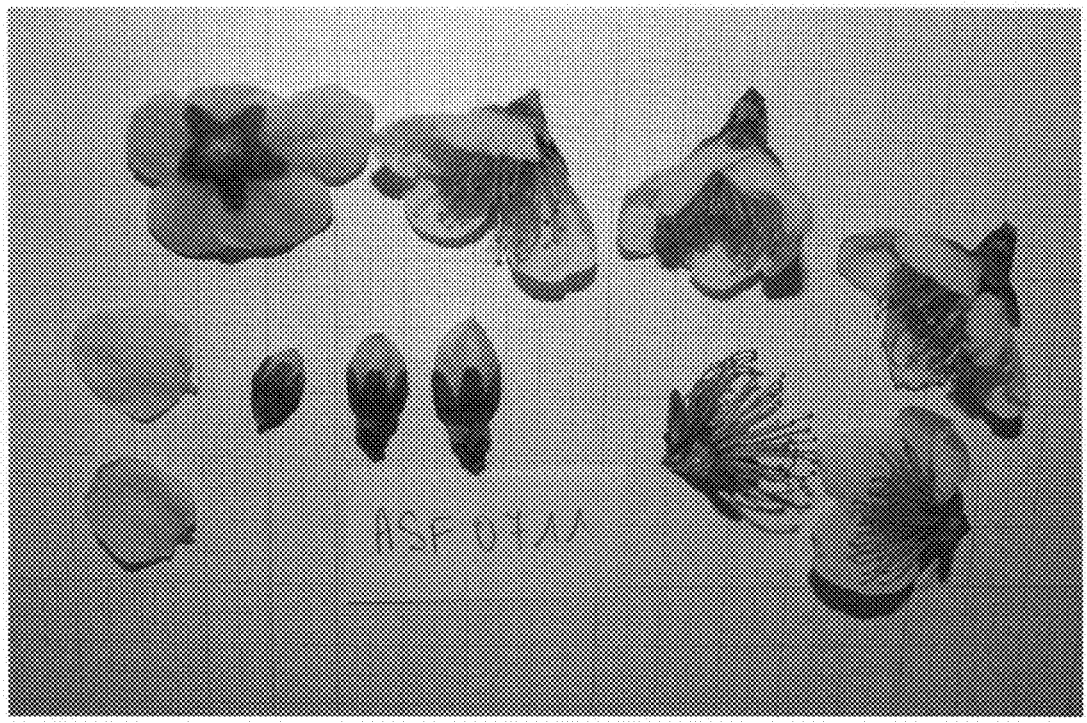
FIG. 4 is a color photograph with reverse and side views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition.

Trees are moderately vigorous and of medium stature, half-standing in a semi-spread to semi-upright out aspect. The anthocyanic coloration of the flowering shoot is present excluding brushwood side away from sun. Flowering begins semi-early to semi-late in springtime. The type of flower is showy with generally medium to large petals of medium pink color. Leaf glands are present and reniform. Time of maturity for consumption is semi-late. The fruit flesh is yellow with slight red pigmentation into stone cavity. Fruit skin color features an homogeneous bright purple red blush. Fruit taste is semi-sweet, aromatic and with a high level of sugars.

The 'NECTAVANTOP' variety ripens almost at the same time and blooms about 6 days after the 'Nectapink' (U.S. Plant Pat. No. 17,584) variety. However, 'NECTAVANTOP' fruits are more appealing, rounder, more regular in shape, with a better red blush coverage of better intensity and with a better taste, more aromatic.

The new variety male parent, which is 'Nectalady' (U.S. Plant Pat. No. 17,580), comparatively ripens later, at the beginning of September, being a variety of the late season of maturity. This variety was interesting as a parent because of its high fruit productivity. Moreover 'Nectalady' fruits are appealing and have a very good aromatic taste.

The new variety female parent, which is 'Redlatenecta' (non-patented), comparatively ripens later, at the beginning of September, being a variety of the late season of maturity. 'Redlatenecta' produce appealing fruits of medium size, with a balanced taste.

DETAILED DESCRIPTION

Referring more specifically to the pomological details of this new and distinct variety of nectarine tree, the following was observed on trees in their second growing season under the ecological conditions prevailing at the orchards located near the town of Elne, Pyrénées-Orientales departement, France. All observations have been done on rootstock cultivars. Used rootstocks were 'Franc Inra Montclar' (non-patented) trees or 'Cadaman' (non-patented) trees or 'INRA GF 677' (non-patented) trees. All major color code designations are by reference to The R.H.S. Colour Chart (Fourth Edition) provided by The Royal Horticultural Society of Great Britain.

Tree:

*Size.*—Generally.— Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigour.*—Considered average.

*Productivity.*—Very productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

*Bearer.*—Very regular. Fruit set has been heavy during the years of observation and thinning of 1 fruit on 3 was necessary every year.

*Form.*—The 'NECTAVANTOP' variety has naturally a semi-spread to semi-upright shape.

*Density.*—Considered dense.

*Hardiness.*—The present tree was grown and evaluated in France. The variety appeared to be hardy under typical central Pyrénées-Orientales departement climatic conditions and was selected partly because of its hardiness. Experimentations on different sites with winter chilling requirement comprised between 350 and 1200 hours showed a good behavior of the tree in all cases. Ascertained temperatures as low as −12 degrees Celsius in winter caused no damages to the tree. The tree was also very resistant to frosty springtime weather.

Trunk:

*Diameter.*—Approximately between 5.5 and 6.5 cm in diameter when measured at a distance of approximately 30 cm above the soil level.

*Bark texture.*—Considered rough.

*Lenticels.*—Numerous lenticels are present. The lenticels range in size from approximately 0.2 to 0.4 cm in width, and about 0.15 cm in height.

*Lenticel color.*—The outside of lenticels has a silver-grey color (RHS Grey 201 C), whereas the inside is considered brown (RHS Greyed Orange 166 B).

*Bark coloration.*—The bark has a silver-grey color (RHS Grey 201 C or RHS Black 202 C).

Branches:

*Size.*—Mature branches as well as current season shoots are medium for the variety.

*Diameter.*—Average as compared to other nectarine varieties. The current season shoots have a diameter from 5.0 to 7.0 millimeters, and branches of trees have a diameter comprised between 12.0 and 18.0 millimeters.

*Surface texture.*—Average, several years old wood has no furrowed appearance.

*Crotch angles.*—Primary branches are considered variable, but the crotch angles are generally between 50 and 60 degrees from the horizontal axis. This particular characteristic is not considered distinctive of the variety, however.

*Current season shoots.*—Surface texture.— Substantially glabrous.

*Internode length.*—Generally 25.0 to 35.0 millimeters.

*Color of mature branches.*—Medium brown (RHS Grey Brown 199 A to B).

*Current seasons shoots.*—Color.— The color of new shoot tips is considered a light yellow green (varying from RHS Yellow Green 144 A to RHS Yellow Green 144 C) on lower part of new shoot tips, whereas the upper part is colored in purple brown to red brown (RHS Greyed Purple Group 187 A to B or RHS Greyed Red 182 A).

Leaves:

*Size.*—Considered medium to large for the species. The ratio leaf length/leaf width is above 4.

*Leaf length.*—Approximately 140 to 165 millimeters with petiole.

*Leaf width.*—Approximately 32 to 52 millimeters.

*Leaf base shape.*—Concave.

*Leaf form.*—Lanceolate.

*Leaf tip form.*—Small and acuminate.

*Leaf color.*—Upper leaf surface.— Dark Green (RHS Green 137 A). Lower surface.— Medium Green (RHS Green 137 B to 137 C).

*Leaf texture.*—Smooth and glabrous.

*Leaf venation.*—Pinnately veined.

*Mid-vein.*—Color.— Generally a Light yellow green (RHS Yellow Green 145 D to 145 C).

*Leaf margins.*—Slightly undulating.

*Form.*—Considered slightly dentate.

*Uniformity.*—Leaves are isolated or grouped by 2 or 3. In this last case, it is found one leaf of normal size with one or two smaller leaves (50% smaller at least).

*Leaf petioles.*—Size.— Considered medium. Length.— About 8.0 to 11.0 mm. Diameter.— About 1.5 mm. Color.— Light yellow green (RHS Yellow Green 144 D to 144 C).

*Leaf glands.*—Size.— Considered medium, about 1.2 mm. Number.— Generally 2. Type.— Reniform. Color.— On young leaves, leaf glands color is considered a pale green (RHS Green 144 B to A). On older leaves, leaf glands color turn to a dark brown (RHS Grey Brown 199 A to 199 B).

*Leaf stipules.*—Generally.— No leaf stipules were observed. But as seen in the characteristic relative to the leaves uniformity, it is possible to find leaves by groups of 2 or 3, with a normal-size leaf and smaller ones.

Flowers:

*Flower buds.*—Generally.—At pre-floral stage of development, the floral buds are conic in form with a round tip. Their form is evolving until blooming, with variables dimensions. Just before blooming, floral buds are approximately 11.0 millimeters wide and approximately 18.0 millimeters long.

*Flower buds.*—Color.—This characteristic is dependent upon the proximity to bloom. At pre-floral stage of development, the bottom of the flowers buds, formed by sepals, is of purple-brown color (Generally RHS Greyed Purple 183 A); the corolla, formed by petals, is generally of medium pink color (varying from RHS Red Purple 65 A to C). Petals color shows an evolution until the end of flowering. The buds are considered hardy under typical central Pyrénées-Orientales departement climatic conditions.

*Hardiness.*—No winter injury was noted during the last several years of evaluation in the central Pyrénées Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—Generally March. The first bloom was observed on Mar. 5, 2003.

*Blooming time.*—Considered semi-early to semi-late in relative comparison to other commercial nectarine cultivars grown in the Pyrénées-Orientales departement, France. The date of full bloom is observed in March, more particularly between March 5$^{th}$ and March 16$^{th}$. The date of bloom varies slightly with climatic conditions and cultural practices. Last observed blooming times were from Mar. 4, 2007 to Mar. 16, 2007, then from Feb. 28, 2008 to Mar. 6, 2008, then from Mar. 7, 2009 to Mar. 16, 2009.

*Duration of bloom.*—Approximately 12 days. This characteristic varies slightly with the prevailing climatic conditions.

*Flower type.*—The variety is considered to have showy type flowers.

*Flower size.*—Considered large. Flower diameter at full bloom is approximately between 34.0 to 40.0 millimeters.

*Bloom quantity.*—Considered good, approximately 40 flowers per meter.

*Flower bud frequency.*—Generally 2 flower buds appear per node, occasionally 1.

*Petal size.*—Generally.— Considered medium to large for the species.

*Length.*—Generally between 20.0 millimeters.

*Width.*—Generally between 19.0 millimeters.

*Petal form.*—Rounded.

*Petal count.*—Generally 5.

*Petal texture.*—Smooth and glabrous.

*Petal color.*—Medium Pink (RHS Red Purple 65 B to C) slightly darkening over time.

*Fragrance.*—Slight.

*Petal claw.*—Form.— The claw is considered to have a conic form with a slighty rounded extremity. Length.— Approximately between 5.0 and 7.0 millimeters. Width.— Approximately 4.0 to 5.0 millimeters.

*Petal margins.*—Generally slightly undulated.

*Petal apex.*—Generally.— The petal apices have a large dome-shaped form.

*Flower pedicel.*—Length.— Considered medium to long and having an average length of approximately 3.0 to 5.0 millimeters. Diameter.— Approximately 2.0 millimeters. Color.— A medium brown (RHS Grey Brown N199 B to 199 C).

*Floral nectaries.*—Color.— A flat golden orange (approximately RHS Greyed Red 178 C to B).

*Calyx.*—Internal surface texture — Smooth and glabrous. Color.— The outer surface of the calyx is considered of Purple-brown (RHS Greyed Purple 183 A) color.

*Sepals.*—Surface texture.— The outer surface has a fine pubescent texture. Size.— Generally medium. Color.— Red (Approximately RHS Greyed Red 178 A).

*Average number of stamens per flower.*—About 40 stamens per flower.

*Anthers.*—Generally.— Medium in length. Color.— Red to orange-red color (approximately RHS Greyed Purple Group 178 A). Anthers are becoming yellow at maturity.

*Pollen production.*—Pollen is abundant, and has a yellow color (Approximately RHS Yellow Orange 17 B to C). The present variety is considered self fruitful (self-pollinating).

*Filaments.*—Size.— Variable in length, approximately 9.0 to 16.0 millimeters in length. Filaments length is generally longer or equal to pistil's length.

*Color.*—Considered light pink (varying from RHS Red Purple 62 C to D) darkening over time.

*Pistil.*—Number.— Usually 1. Generally.— Medium in size. Length.— Approximately 16.0 to 19.0millimeters including the ovary; Generally approximately equal or smaller than filament's length. Color.— Considered a very pale green (RHS Yellow Green 150 D Group or RHS Yellow Green 151 D Group). Surface texture.— The variety has a glabrous pistil.

Fruit:

*Maturity when described.*—Very firm ripe condition (shipping ripe).

*Date of first picking.*—Aug. 3, 2003. The picking generally occurs between August 1$^{st}$ and August 10$^{th}$ under normal climatic conditions. The date of harvest varies slightly with the prevailing climatic conditions.

*Date of last picking.*—Aug. 13, 2003. Picking can generally be achieved with only 2 harvests within approximately 12 days. Last known picking times were from Aug. 1$^{st}$, 2006 to Aug. 8, 2006, then from Aug. 2, 2007 to Aug. 8, 2007, then from Jul. 30, 2008 to Aug. 12, 2008, then from Aug. 2, 2009 15 to Aug. 14, 2009.

*Size.*—Generally.— Considered large, and homogenous between fruits.

*Average cheek diameter.*—Approximately 72.0 to 75.0 millimeters.

*Average axial diameter.*—Approximately 68.0 to 75.0 millimeters.

*Typical weight.*—Approximately between 250.0 and 300.0 grams. This characteristic is high dependent upon the prevailing cultural practices, and therefore is not particularly distinctive of the variety.

*Fruit form.*—Generally.— Round to slightly oblate. The fruit is generally uniform in symmetry viewed from the suture's plane.

*Fruit suture.*—Very shallow and smooth, extending from the base to the apex. No apparent callousing or stitching exists along the suture line.

*Suture.*—Color.— This has generally a color similar to the whole fruit color, a dark red blush (RHS Greyed Purple 185 A) over a orange-red ground (Varying from RHS Orange Red N 34 A to RHS Orange Red 34 B).

*Ventral surface.*—Form.— Smooth.

*Apex.*—Non-prominent, small, and generally slightly depressed.

*Base.*—Wide-mouthed, shallow.

*Stem cavity.*—Average depth of the stem cavity is about 0.8 cm. Average width is about 1.5 cm.

*Fruit skin.*—Thickness.— Considered very thick and strong, and very tenacious to the flesh to tenacious to the flesh depending on stage of maturity. Texture.— Glabrous. Taste.— Semi-sweet with a high level of sugar, aromatic. Tendency to crack.— None observed.

*Color.*—Blush color.— This blush color is generally a bright purple red blush (RHS Red Purple 59 A to RHS Red Purple 46 A). The red blush covers between 80% and 90% of the fruit skin surface. Ground color.— Orange-red ground (Varying from RHS Orange Red N 34 A to RHS Orange Red 34 B) on about 10% to 20% of the fruit skin surface.

*Fruit stem.*—Medium in length, approximately 5.0 millimeters.

*Diameter.*—Approximately 4.0 millimeters.

*Color.*—Pale green (RHS Yellow Green 145A to 145 B).

*Flesh.*—Ripens.— Very evenly, homogenous, long shelf-life of the fruit. Texture.— Very firm, very dense, juicy at harvest maturity stage. Fibers.— No fibers. Aroma.— Pronounced. Eating quality.— Considered very good and aromatic. Flavor.— Considered semi-sweet. The Brix is generally superior to 13.0 degrees. Acidity is comprised between 6 and 9 meq/100ml. The flavor is considered aromatic. The flesh is juicy. Juice.— Very juicy at complete maturity. Brix.— Generally superior to 13.0 degrees. This characteristic varies slightly with the number of fruit per tree, the prevailing cultural practices and the surrounding climatic conditions. Flesh color.— Generally Yellow Orange (RHS Yellow Orange 16 B to C). There is generally no red pigmentation under the skin. However, depending on the stage of maturity, a very slight red pigmentation can appear on the flesh. Flesh is generally red inside the stone cavity and star-shapedly arranged over about 1 cm around the stone cavity.

Stone:

*Type.*—Clingstone.

*Size.*—Considered medium to large for the variety. The stone size varies significantly depending upon the tree vigor, crop load and prevailing growing conditions.

*Length.*—Approximately 28 to 32.0 millimeters.

*Width.*—Approximately 19 to 22.0 millimeters.

*Diameter.*—Approximately 16 to 18.0 millimeters.

*Form.*—Elliptic.

*Base.*—Straight.

*Apex.*—Shape.— The stone apex has a small sharp tip.

*Stone cavity.*—Considered medium to large-sized, with an elliptic-form. Stone cavity's dimensions correspond to the stone's dimensions.

*Stone surface.*—Surface texture.— The pit is transversely furrowed on its entire surface. Furrows are more pronounced toward the apex. The stone is pitted toward the base. Relief is generally prominent and present basally. Ridges.— The surface texture is generally characterized by more prominent ridges along the ventral edges and is more prominent at the apical tip.

*Ventral edge.*—Width.— Considered small to medium, and having a dimension of approximately 2.0 millimeters at mid-suture.

*Dorsal edge.*—Shape.— Grooved.

*Stone color.*—The color of the dry stone is generally a light orange-brown (RHS Greyed Orange 166 A to D).

*Tendency to split.*—Splitting is generally absent.

*Kernel.*—Size.— The kernel is considered medium. Length.— About 20.0 millimeters. Width.— About 12.0 millimeters. Thickness.— About 3.0 to 4.0 millimeters. Form.— Considered flattened and elliptic. Pellicle.— Slightly pubescent. Color.— The kernel skin is brown-orange (RHS Greyed Orange 167 C) with darker brown-orange streaks (RHS Greyed Orange 166 C). The almond, which is the seed of the kernel, is cream-white (RHS Orange White 159 D). The kernel and its embryo are mature at the time of fruit maturity.

*Use.*—The subject variety 'NECTAVANTOP' is considered to be a nectarine tree of the semi-late season of maturity, which produces aromatic semi-sweet fruit with a brix higher than 13 degrees. Fruits are excellent for uncooked consumption, crunchy or at full maturity. Due to their flesh quality, firmness and density, they can also be commercialized as $4^{th}$ range product (packed fruit or fruit in bags for example). They are also useful for both local and very long distance shipping because they have a long shelf life after harvesting, up to 1 month.

*Keeping quality.*—Remarkable. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

*Shipping quality.*—Considered very good. Fruits of the new nectarine variety showed minimal bruising of the flesh or skin damage after being subjected to normal harvesting and packing procedures. Its resistance to handling during harvest and packing and its long shelf life without alteration after harvest easily permit 3 to 4 weeks shipping at 2 degrees Celsius.

*Resistance to insects and disease.*—No particular susceptibilities were noted. Under our climatic conditions, favourable to powdery mildew, and with few treatments, the present variety has not been shown to be very sensitive to powdery mildew, or conservation diseases and decay due to its thick and strong skin. No bacteriostatic substances were applied, and no symptom was observed.

Although the new variety of nectarine tree possesses the described characteristics when grown under the ecological conditions prevailing near the town of Elne, France, it should be understood that variations of the usual magnitude and characteristics incident to changes in growing conditions, fertilization, pruning, pest control and horticultural management are to be expected.

We claim:

1. A new and distinct variety of nectarine tree as illustrated and described, characterized by fruits of very long shelf life without alteration before and after harvesting, with a semi-sweet yellow flesh of high eating quality and an attractive skin, with a very high percentage of red blush.

* * * * *